United States Patent [19]

Schermanz et al.

[11] Patent Number: 5,196,545
[45] Date of Patent: Mar. 23, 1993

[54] PROCESS FOR THE PREPARATION OF ALLANTOIN

[75] Inventors: Karl Schermanz, Graz; Klaus Fitzinger, Linz, both of Austria

[73] Assignee: Chemie Linz Gesellschaft m.b.H., Linz, Austria

[21] Appl. No.: 714,281

[22] Filed: May 30, 1991

[30] Foreign Application Priority Data

Jun. 5, 1990 [AT] Austria ............................ A 1210/90

[51] Int. Cl.$^5$ ............................................ C07D 233/88
[52] U.S. Cl. ................................................... 548/318.1
[58] Field of Search ......................................... 548/311

[56] References Cited

U.S. PATENT DOCUMENTS

| | | | |
|---|---|---|---|
| 2,158,098 | 5/1939 | Zellner et al. | 548/311 |
| 4,692,547 | 9/1987 | Driscoll et al. | 560/186 |
| 4,814,491 | 3/1989 | Driscoll et al. | 560/186 |

FOREIGN PATENT DOCUMENTS

| | | |
|---|---|---|
| 0099981 | 2/1984 | European Pat. Off. . |
| 1939924 | 2/1971 | Fed. Rep. of Germany . |
| 2717698 | 5/1978 | Fed. Rep. of Germany . |
| 128099 | 11/1977 | German Democratic Rep. . |
| 139427 | 12/1978 | German Democratic Rep. . |

OTHER PUBLICATIONS

"Chemical Abstracts", vol. 97, entry 55807b (1982).
"Chemical Abstracts", vol. 97, entry 92275x (1982).
"Tetrahedron", 33, 1191–1196 (1977).

*Primary Examiner*—Patricia L. Morris
*Assistant Examiner*—Lenora Miltenberger
*Attorney, Agent, or Firm*—Wenderoth, Lind & Ponack

[57] ABSTRACT

Process for the preparation of allantoin in a two-stage reaction by reaction of methyl glyoxylate methyl hemiacetal with urea in the presence of an inorganic acid at a pH-value of 1.0–2.0 and carrying out the ring-closure reaction at a pH-value of 7.0 to 9.0 in a second reaction stage.

3 Claims, No Drawings

PROCESS FOR THE PREPARATION OF ALLANTOIN

The invention relates to a process for the preparation of allantoin.

Allantoin (2,5-dioxo-4-imidazolinyl) urea and its salts and metal complexes are pharmaceutically active compounds which are used in the therapy and prophylaxis of cancer.

DE-A 19 39 924 discloses a process for the preparation of allantoin in aqueous medium, in which glyoxylic acid and urea are reacted in the presence of a mineral acid or of an organic sulfonic acid, resulting in allantoin in yields of less than 60%.

A process for the preparation of allantoin by reaction of glyoxylic esters with urea in the presence of a condensing agent in acid or basic medium is described in Chemical Abstracts, Vol. 97, 55807. 0.5–4.0 equivalents of condensing agent are employed per equivalent of glyoxylic ester. Furthermore, a process for the preparation of allantoin by reaction of an acetic acid derivative with urea in the presence of a condensing agent in acid or basic medium is disclosed in Chemical Abstracts, Vol. 97, 92275. 0.1 to 4.0, but preferably 0.5–4.0, equivalents of condensing agent are employed per equivalent of acetic acid derivative.

Both processes provide allantoin in a yield of 67–76% in a one-stage reaction which is carried out either in acid or in basic medium. In both processes a large amount of condensing agent is used, and it remains in the waste water after the isolation of the allantoin and must be neutralized. Application of these processes on an industrial scale is therefore possible only with difficulty.

It has now been possible, unexpectedly, to find a process for the preparation of allantoin which can be applied on the industrial scale, in which allantoin can be obtained in high yield and with high purity, starting from methyl glyoxylate methyl hemiacetal, using catalytic amounts of inorganic acid in a reaction which is initially acidic and then basic.

The invention accordingly relates to a process for the preparation of (2,5-dioxo-4-imidazolinyl)urea (allantoin) of the formula

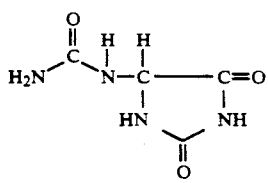

comprising reacting
a) methyl glyoxylate methyl hemiacetal of the formula

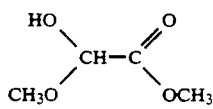

with urea in the presence of catalytic amounts of an inorganic acid at a pH-value of 1.0–2.0 to give a compound of the formula

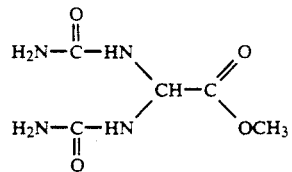

and then carrying out
b) the ring-closure reaction at a pH-value of 7.0–9.0.

The methyl glyoxylate methyl hemiacetal used as starting compound is known. The compound is easy to obtain and can be prepared in a straightforward manner, for example as described in EP-B 0 099 981.

The reaction is carried out in a two-stage process without isolation of the intermediate of the formula III. This entails initially methyl glyoxylate methyl hemiacetal being reacted with urea in the presence of catalytic amounts of an inorganic acid and, where appropriate, in the presence of an inert diluent. The starting compounds are normally employed in stoichiometric amount, that is to say 2 mol of urea are employed per mol of methyl glyoxylate methyl hemiacetal. However, it may be advantageous for completion of the reaction to employ an up to 2 molar excess of urea.

Employed as condensing agents are inorganic mineral acids, for example hydrochloric acid or sulfuric acid, preferably sulfuric acid. This entails 0.02–0.1 mol, preferably 0.03–0.07 mol, of acid being employed per mol of methyl glyoxylate methyl hemiacetal.

The reaction can, where appropriate, be carried out in the presence of a diluent which is inert under the reaction conditions. Suitable inert diluents are lower aliphatic alcohols, preferably methanol. The reaction is carried out at reaction temperatures of about 50°–80° C.

After a reaction time of about 30 min–2 hours, where appropriate some of the diluent is removed by distillation and then the reaction mixture is cooled slightly and, in order to carry out the second reaction stage, a base, for example sodium hydroxide solution, potassium hydroxide solution, piperidine or triethylamine, preferably dilute sodium hydroxide solution or potassium hydroxide solution, is added until the pH-value is 7.0–9.0. The reaction mixture is then again heated to the boiling point. Where appropriate the pH-value is kept in the above-mentioned range during this by further metering in of alkali.

After the reaction is complete, the product is isolated in a customary manner, for example by filtration, centrifugation or the like, from the reaction solution. Allantoin is obtained in yields of up to 85% and in high purity by the process according to the invention.

EXAMPLE 1

A 1200 l enamelled tank with anchor stirrer and descending condenser was charged while stirring with 324 kg of methyl glyoxylate methyl hemiacetal, 120 kg of methanol, 540 kg of urea orills and 135 kg of 8% strength sulfuric acid in this order. The pH-value of the mixture is 1.5–1.8.

The tank was then closed and heated to 70° C. over the course of 1 hour. The mixture began to boil vigorously at about 70° C.

As soon as the mixture stopped boiling the temperature was raised again slightly and a total of about 60 l of methanol was distilled out, the boiling point of the mixture rose to about 75° C. After a reaction time of about 1 hour at this temperature, the mixture was slightly cooled and adjusted to a pH-value of 7.3 with 97 kg of 20% strength NaOH. It was again heated to the boiling point and the pH-value was kept at between 7.5 and 8 for 2 hours by further addition of NaOH.

The reaction mixture was cooled while stirring to at least 20° C. and then centrifuged and washed with water. The product moist from centrifugation was dried in vacuo.

Total yield: 359 kg=84.1% of theory
Purity: Content: 99.6% by acidimetry,
Sulfate: <100 ppm,
Melting point 220°-223° C.,
Sulfated ash: <0.1%.

What we claim is:

1. Process for the preparation of (2,5-dioxo-4imidazolinyl)urea (allantoin) of the formula

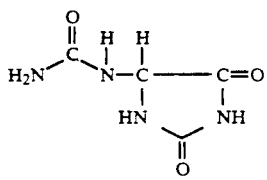

comprising reacting a) methyl glyoxylate methyl hemiacetal of the formula

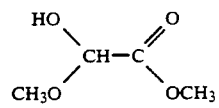

with urea in the presence of catalytic amounts of an inorganic acid at a pH-value of 1.0–2.0 to give a compound of the formula

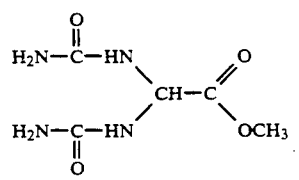

and then carrying out b) the ring-closure reaction at a pH-value of 7.0–9.0.

2. Process according to claim 1, comprising employing in stage a) 0.02–0.1 mol of inorganic acid per mol of methyl glyoxylate methyl hemiacetal.

3. Process according to claim 1, comprising employing sulfuric acid as inorganic acid in stage a).

* * * * *